US010617854B2

(12) United States Patent
Pillai

(10) Patent No.: US 10,617,854 B2
(45) Date of Patent: Apr. 14, 2020

(54) TRANS-JUGULAR CAROTID ARTERY ACCESS METHODS

(71) Applicant: Vascular Access Technologies, Inc., South Jordan, UT (US)

(72) Inventor: Lakshmikumar Pillai, Morgantown, WV (US)

(73) Assignee: Vascular Access Technologies, Inc., South Jordan, UT (US)

( * ) Notice: Subject to any disclaimer, the term of this patent is extended or adjusted under 35 U.S.C. 154(b) by 203 days.

(21) Appl. No.: 15/835,114

(22) Filed: Dec. 7, 2017

(65) Prior Publication Data
US 2018/0161551 A1    Jun. 14, 2018

Related U.S. Application Data

(60) Provisional application No. 62/432,369, filed on Dec. 9, 2016, provisional application No. 62/433,634, filed on Dec. 13, 2016, provisional application No. 62/440,735, filed on Dec. 30, 2016.

(51) Int. Cl.
| | | |
|---|---|---|
| A61M 25/10 | (2013.01) |
| A61M 25/00 | (2006.01) |
| A61M 25/01 | (2006.01) |
| A61M 25/09 | (2006.01) |

(52) U.S. Cl.
CPC ...... *A61M 25/104* (2013.01); *A61M 25/0082* (2013.01); *A61M 25/0032* (2013.01); *A61M 25/0102* (2013.01); *A61M 25/09041* (2013.01); *A61M 2025/0095* (2013.01); *A61M 2025/0183* (2013.01)

(58) Field of Classification Search
CPC ............ A61M 25/104; A61M 25/0082; A61M 25/0032; A61M 25/0102; A61M 25/09041; A61M 2025/0183; A61M 25/09; A61M 25/0662
USPC ......... 604/510; 606/200, 127, 129, 182, 195
See application file for complete search history.

(56) References Cited

U.S. PATENT DOCUMENTS

| | | |
|---|---|---|
| 4,559,039 A | 12/1985 | Ash et al. |
| 4,790,825 A | 12/1988 | Bernstein et al. |
| 4,966,163 A | 10/1990 | Kraus et al. |

(Continued)

FOREIGN PATENT DOCUMENTS

| | | |
|---|---|---|
| WO | 2004018029 | 3/2004 |
| WO | 2005053547 | 6/2005 |

(Continued)

OTHER PUBLICATIONS

Notice of Allowance dated Jan. 28, 2019 for U.S. Appl. No. 14/949,243.

(Continued)

*Primary Examiner* — Bhisma Mehta
*Assistant Examiner* — Nidah M Hussain
(74) *Attorney, Agent, or Firm* — Stoel Rives LLP

(57) ABSTRACT

Methods and devices for trans-jugular carotid access are disclosed. Methods within the scope of this disclosure include methods of trans-jugular carotid access originating in the leg of a patient or other location remote to the jugular vein and carotid artery and methods originating at the neck of a patient. Devices used in connection with the disclosed methods may comprise access catheters, lumens, and stylets.

19 Claims, 15 Drawing Sheets

(56) References Cited

U.S. PATENT DOCUMENTS

| | | |
|---|---|---|
| 5,421,348 A | 6/1995 | Larnard |
| 5,492,530 A | 2/1996 | Fischell et al. |
| 5,685,820 A | 11/1997 | Riek et al. |
| 5,733,248 A | 3/1998 | Adams et al. |
| 6,047,700 A | 4/2000 | Eggers et al. |
| 6,102,926 A | 8/2000 | Tartaglia et al. |
| 6,190,353 B1 | 2/2001 | Makower et al. |
| 6,217,527 B1 | 4/2001 | Selmon et al. |
| 6,475,226 B1 | 11/2002 | Belef et al. |
| 6,508,777 B1 | 1/2003 | Macoviak et al. |
| 6,554,794 B1 | 4/2003 | Mueller et al. |
| 6,623,480 B1 | 9/2003 | Kuo et al. |
| 6,709,444 B1 | 3/2004 | Makower |
| 6,726,677 B1 | 4/2004 | Flaherty et al. |
| 6,955,657 B1 | 10/2005 | Webler |
| 7,008,979 B2 | 3/2006 | Schottman et al. |
| 7,374,567 B2 | 5/2008 | Heuser |
| 7,648,517 B2 | 1/2010 | Makower et al. |
| 8,019,420 B2 | 9/2011 | Hine et al. |
| 8,241,311 B2 | 8/2012 | Ward et al. |
| 8,374,680 B2 | 2/2013 | Thompson |
| 8,409,236 B2 | 4/2013 | Pillai |
| 8,568,435 B2 | 10/2013 | Pillai et al. |
| 9,220,874 B2 | 12/2015 | Pillai et al. |
| 2001/0012924 A1 | 8/2001 | Milo et al. |
| 2001/0023346 A1 | 9/2001 | Loeb |
| 2002/0004666 A1 | 1/2002 | Schwager et al. |
| 2002/0029060 A1 | 3/2002 | Hogendijk et al. |
| 2002/0120250 A1 | 8/2002 | Altman |
| 2002/0122877 A1* | 9/2002 | Harish .............. A61L 31/10 427/2.24 |
| 2002/0133168 A1 | 9/2002 | Smedley et al. |
| 2002/0169377 A1 | 11/2002 | Khairkhahan et al. |
| 2003/0040771 A1* | 2/2003 | Hyodoh ............ A61F 2/90 606/200 |
| 2004/0039371 A1 | 2/2004 | Tockman et al. |
| 2004/0059280 A1 | 3/2004 | Makower et al. |
| 2004/0082850 A1 | 4/2004 | Bonner et al. |
| 2004/0133168 A1 | 7/2004 | Salcudean et al. |
| 2004/0181150 A1 | 9/2004 | Evans et al. |
| 2004/0181238 A1 | 9/2004 | Zarbatany et al. |
| 2005/0101984 A1 | 5/2005 | Chanduszko et al. |
| 2005/0149097 A1 | 7/2005 | Regnell et al. |
| 2005/0209579 A1 | 9/2005 | Yacoubian et al. |
| 2006/0009737 A1 | 1/2006 | Whiting et al. |
| 2006/0135962 A1 | 6/2006 | Kick et al. |
| 2006/0173440 A1 | 8/2006 | Lamson |
| 2006/0247750 A1 | 11/2006 | Seifert et al. |
| 2007/0021767 A1 | 1/2007 | Breznock |
| 2007/0203515 A1 | 3/2007 | Heuser et al. |
| 2008/0082136 A1 | 4/2008 | Gaudini |
| 2008/0125748 A1 | 5/2008 | Patel |
| 2008/0154172 A1 | 6/2008 | Mauch |
| 2008/0171944 A1 | 7/2008 | Brenneman et al. |
| 2008/0215008 A1 | 9/2008 | Nance et al. |
| 2008/0249565 A1 | 10/2008 | Michler et al. |
| 2009/0112050 A1 | 4/2009 | Farnan et al. |
| 2009/0240122 A1 | 9/2009 | Avitsian |
| 2010/0249491 A1 | 9/2010 | Farnan et al. |
| 2011/0178530 A1 | 7/2011 | Bly |
| 2011/0295206 A1 | 12/2011 | Gurley |
| 2012/0136247 A1 | 5/2012 | Pillai |
| 2012/0136366 A1 | 5/2012 | Pillai |
| 2013/0006282 A1 | 1/2013 | Wilkinson |
| 2013/0072957 A1* | 3/2013 | Anderson .......... A61M 25/104 606/194 |
| 2013/0324901 A1 | 12/2013 | Pillai |
| 2013/0324967 A1 | 12/2013 | Pillai et al. |
| 2014/0142418 A1 | 5/2014 | Gurley et al. |
| 2014/0142677 A1* | 5/2014 | Heuser .............. A61M 25/0194 623/1.11 |
| 2015/0320357 A1* | 11/2015 | Kuraguntla ............... G01F 1/00 600/505 |
| 2017/0056625 A1 | 3/2017 | Pillai |
| 2019/0321600 A1 | 10/2019 | Pillai |

FOREIGN PATENT DOCUMENTS

| | | |
|---|---|---|
| WO | 2011068540 | 6/2011 |
| WO | 2013119547 | 8/2013 |

OTHER PUBLICATIONS

Notice of Allowance dated Mar. 19, 2019 for U.S. Appl. No. 15/464,055.

Office Action dated Jan. 30, 2018 for U.S. Appl. No. 14/949,243.

Office Action dated May 30, 2017 for U.S. Appl. No. 14/949,243.

Faul, et al., Vascular Disease Management, vol. 5 No. 5 ,Sep./Oct. 2008 ,128-133.

Huang, et al.,Evaluation of the Needle Technique for Producing an Arteriovenous Fistula, Journal of Applied Physiology, vol. 77(6) ,Dec. 1994 ,2907-2911.

Khanna, et al.,sharpening of Hollow Silicon Microneedles to Reduce Skin Penetration Force, ,Mar. 15, 2010 ,045011.

Lumend Inc., et al.,Outback LTD Re-Entry Catheter; Product Resources (http://www.lumend.com/Images/Technology/Products/brochure. pdf), ,Jul. 19, 2006.

Mewissen, et al.,Revascularization of Long FP Arterial Occlusions, Endovascular Today ,Mar. 2004 ,2-4.

O'Callaghan, et al.,Dynamics of Stab Wounds: Force Required for Penetration of Various Cadaveric Himan Tissues, Forensic Sci. Int'l., vol. 104 ,Oct. 11, 1999 ,173-178.

Office Action dated Sep. 7, 2018 for U.S. Appl. No. 15/347,478.

Office Action dated Sep. 27, 2018 for U.S. Appl. No. 15/464,055.

Office Action dated Oct. 2, 2018 for U.S. Appl. No. 14/949,243.

Notice of Allowance dated May 1, 2019 for U.S. Appl. No. 15/347,478.

Office Action dated Oct. 23, 2019 for U.S. Appl. No. 15/834,998.

Office Action dated Jun. 14, 2018 for U.S. Appl. No. 14/949,243.

\* cited by examiner

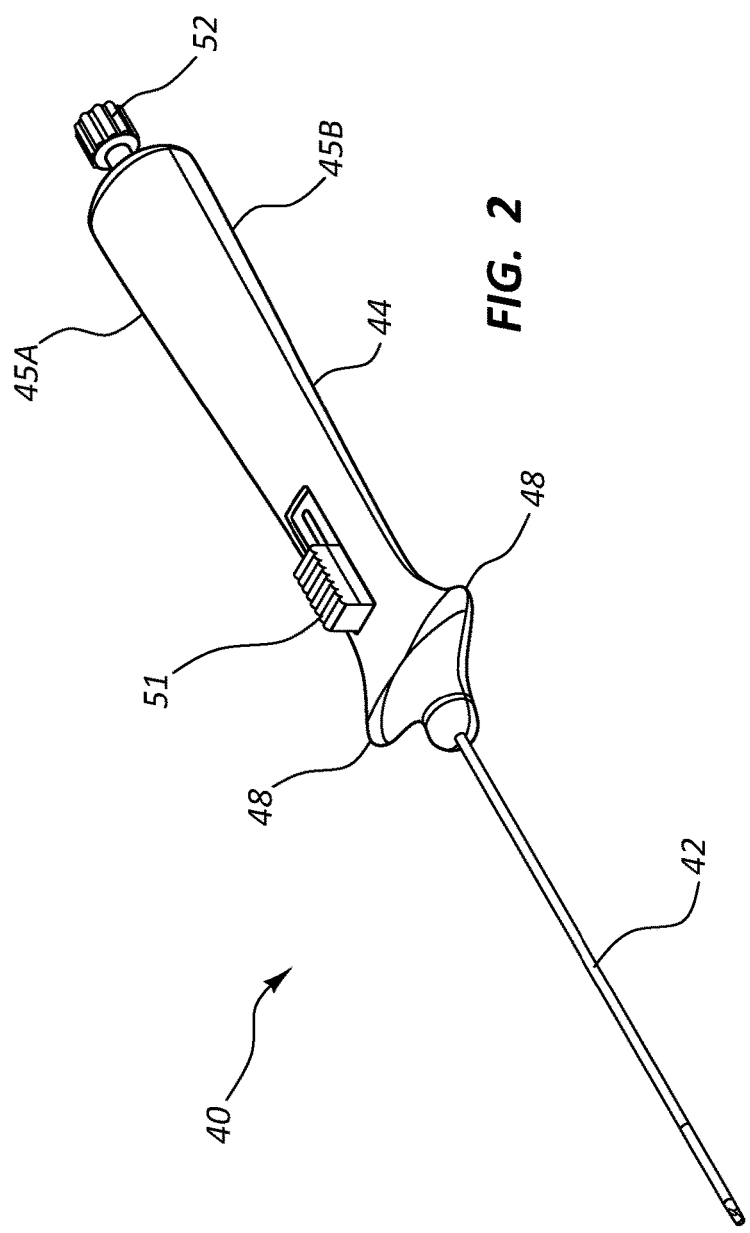
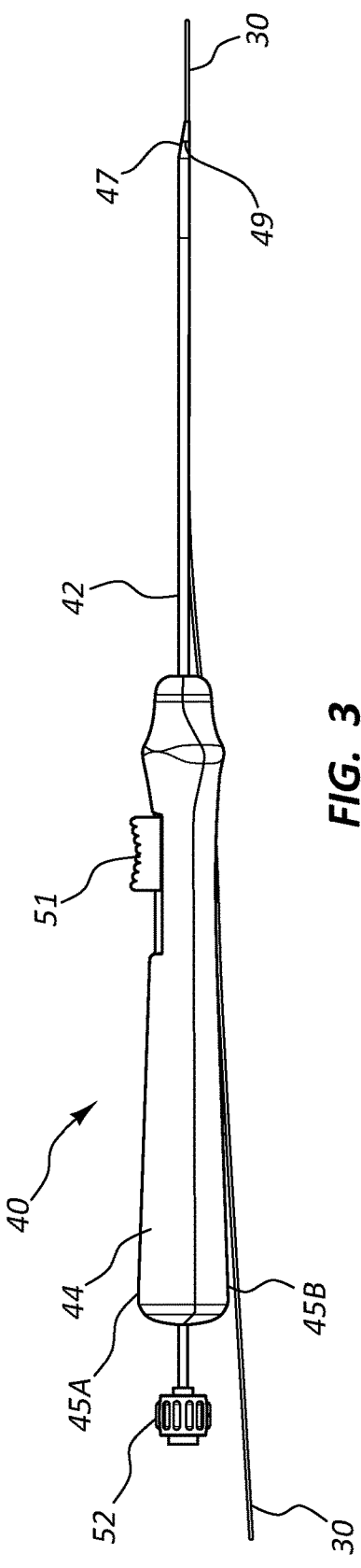
FIG. 2
FIG. 3

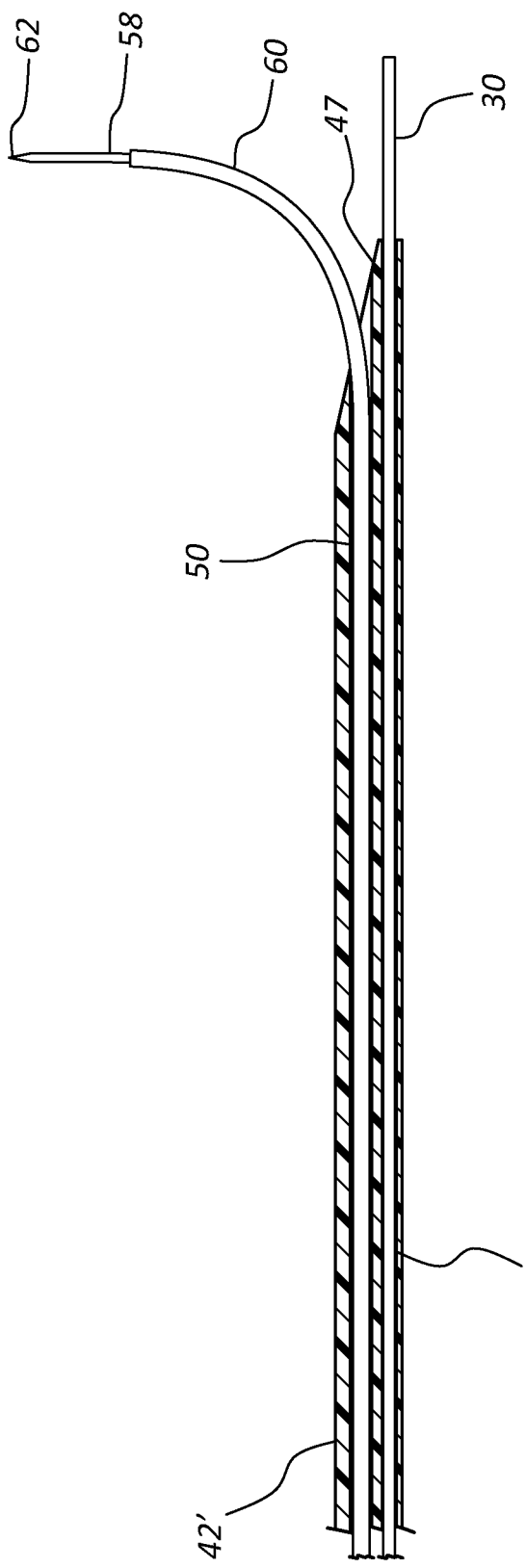
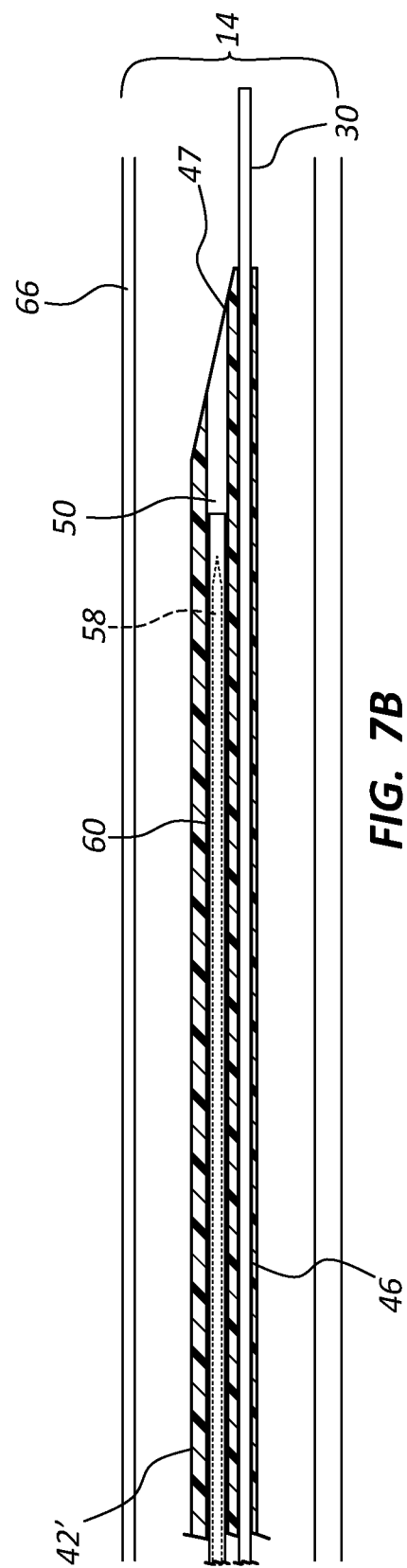
FIG. 7A
FIG. 7B

TRANS-JUGULAR CAROTID ARTERY ACCESS METHODS

RELATED APPLICATIONS

This application claims priority to U.S. Provisional Application No. 62/432,369 filed Dec. 9, 2016, and titled "Trans-Jugular Carotid Artery Access Method," U.S. Provisional Application No. 62/433,634 filed Dec. 13, 2016, and titled "Trans-Jugular Carotid Artery Access Method," and U.S. Provisional Application No. 62/440,735 filed Dec. 30, 2016, and titled "Trans-Jugular Carotid Artery Access Method," all of which are hereby incorporated by reference in their entireties.

TECHNICAL FIELD

The present disclosure relates generally to the field of medical devices. More particularly, some embodiments relate to methods of accessing the carotid artery via the jugular vein to perform treatments on a medical condition.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2 illustrates a perspective view of a transvascular access device accordingly to an embodiment.

FIG. 3 illustrates a side view of the device of FIG. 2 coupled to a guidewire.

FIG. 7A illustrates a cross-sectional schematic view of a device in accordance with an embodiment with the stylet deployed in an actuated configuration.

FIG. 7B illustrates a cross-sectional schematic view of a device in accordance with an embodiment, in a retracted configuration with the stylet retracted, being advanced over a guidewire in a vessel, such as a vein.

DETAILED DESCRIPTION

Figure 1A:
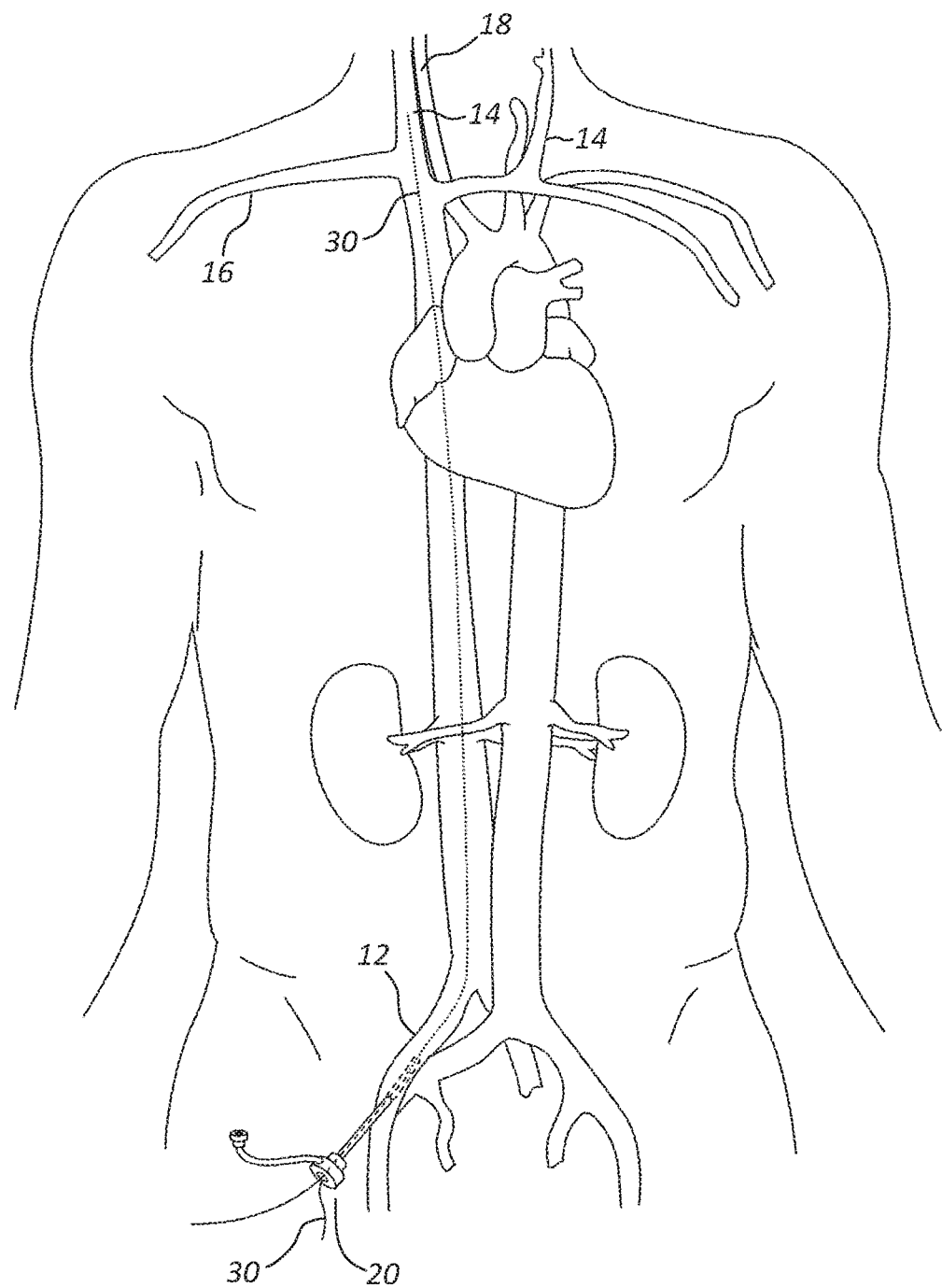
FIG. 1A is a schematic drawing illustrating the insertion of a guidewire extending from a patient's femoral vein to the jugular vein.

Certain medical procedures require access to the carotid artery in order to treat a patient for certain medical conditions. In some procedures the carotid artery is accessed through open surgical procedure. An exemplary procedure that includes open surgery is carotid endarterectomy in which the carotid artery is clamped and cut open and then scraped to remove fatty plaque to treat a blockage in the carotid artery. Very ill and/or elderly patients may have a difficult time tolerating an open surgical procedure under general anesthesia.

Another method of accessing the carotid artery is to access the carotid artery percutaneously via the femoral artery and advancing treatment devices such as catheters through the aortic arch to the carotid artery. One such exemplary procedure is carotid artery invention by advancing a filter and an angioplasty balloon catheter percutaneously (via a sheath) form the femoral artery into the aortic arch and then into the blocked carotid artery under local anesthesia. However, in some patients, the aortic arch may be difficult to navigate due to age-related calcification and/or tortuosity.

The present disclosure includes methods and devices for accessing a patient's carotid artery via the patient's jugular vein, without open surgery or having to pass a treatment device through the patient's aortic arch. It is within the scope of this disclosure to access the carotid artery at a remote access point, e.g., femoral vein, brachial vein, basilic vein, cephalic vein, median antecubital, median antebrachial, etc., or directly though the patient's neck.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. For example, two components may be coupled to each other through an intermediate component. The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end or the end nearest the practitioner during ordinary use.

Figure 1B:
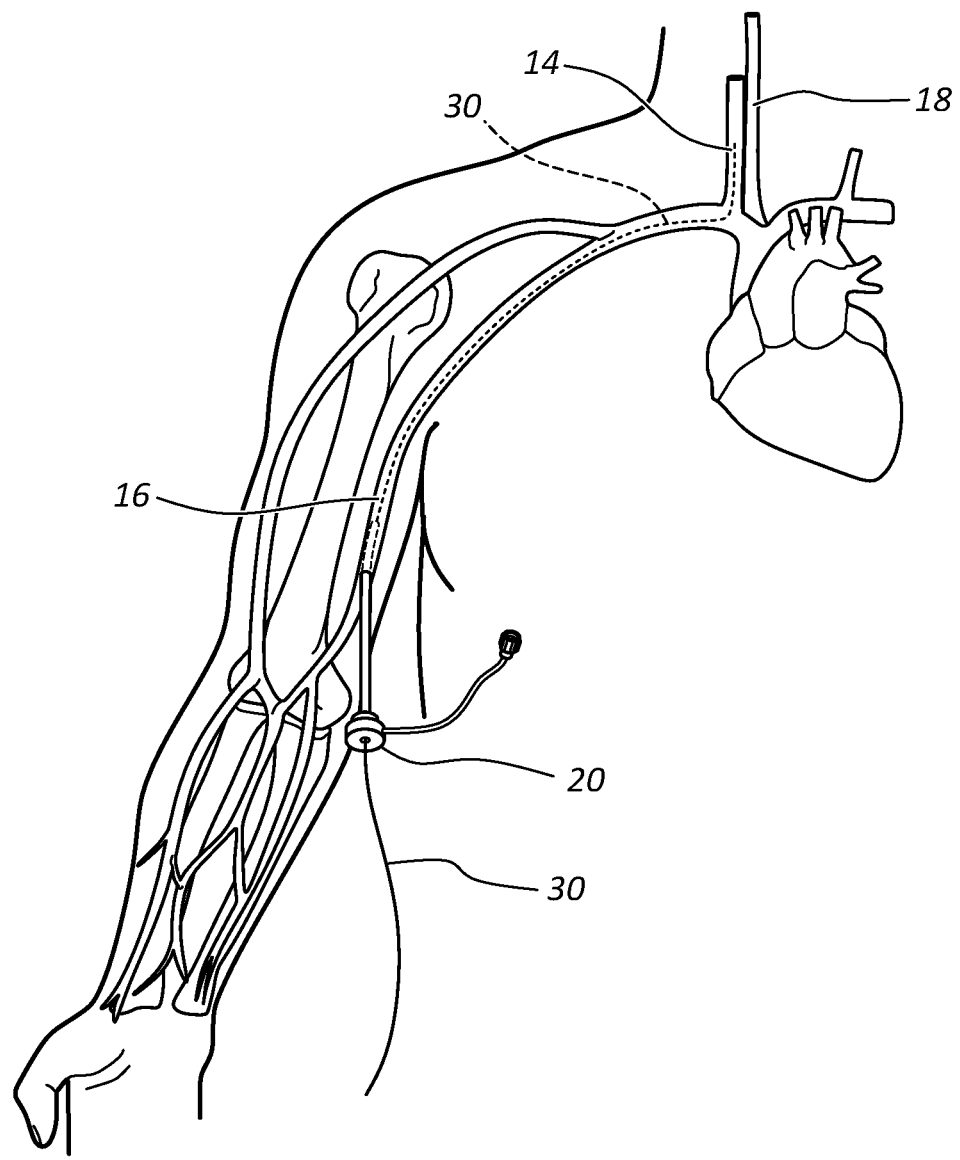
FIG. 1B is a schematic drawing illustrating the insertion of a guidewire extending from a patient's vein in their arm to the jugular vein.

FIG. 1A schematically illustrates the vasculature of a patient wherein the femoral vein 12 has been accessed, such as by the Modified Seldinger Technique. A general use guidewire 30 (such as a guidewire measuring about 0.0035 inches in diameter) may be passed through a vascular sheath 20 and positioned in a right or left jugular vein 14 of the patient via the inferior vena cava. The guidewire 30 may ultimately be positioned in the vicinity of a desired access point to a carotid artery 18. The desired access point may be located at any point along the jugular vein 14 where the jugular vein also runs along the carotid artery 18. For example, the desired access point may be just below the bifurcation of the carotid artery 18 into the internal carotid artery 19 and the external carotid artery 17. In this manner, a medical practitioner may be able to access the carotid artery 18 without having to do an open surgical procedure or to advance percutaneously from the patient's femoral artery and past the patient's aortic arch. Alternatively, the remote entry point may be a vein 16 within the patient's arm (e.g., brachial vein, basilic vein, cephalic vein, median antecubital, median antebrachial, etc.) and the vascular catheter 42 may have a length of about half a meter and a diameter around 7 french, as illustrated in FIG. 1B.

FIGS. 2-6B illustrate an embodiments of an access device 40. A vascular catheter 42 extends distally from a handle 44. The length and diameter of the vascular catheter 42 depends on the distance between a remote entry point and the desired access point to the carotid artery 18. For example, the remote entry point may be the femoral vein 12 and the vascular catheter 42 may have a length of about 1 meter and may have a diameter of around 7 french (0.092 inches).

The vascular catheter 42 may comprise a catheter tip 47 at the distal end of the vascular catheter 42. The catheter tip 47 may be tapered, beveled, conical or comprise other shapes or structures. The catheter tip 47 in FIG. 3 is illustrated as conical. In some embodiments, the vascular catheter 42 may have a guidewire lumen 46, as illustrated in FIGS. 2-6B. The guidewire 30 lumen 46 may be configured to be a rapid exchange (RX) guidewire lumen for receiving the guidewire 30. In embodiments in which the remote entry point is the femoral vein 12 and the desired access point is the carotid artery 18, the guidewire 30 may be a 0.035 inch guidewire. In some embodiments the guidewire 30 is advanced through the handle 44 of the access device 40. In some embodiments the guidewire 30 may be introduced into the guidewire lumen 46 using an introducer kit (not shown). The guidewire 30 may be positioned adjacent to the desired access point in the patient's jugular vein 14. The vascular catheter 42 may be advanced over the guidewire 30 before or after the guidewire 30 is positioned adjacent to the desired access point in the jugular vein 14.

Figure 4A:
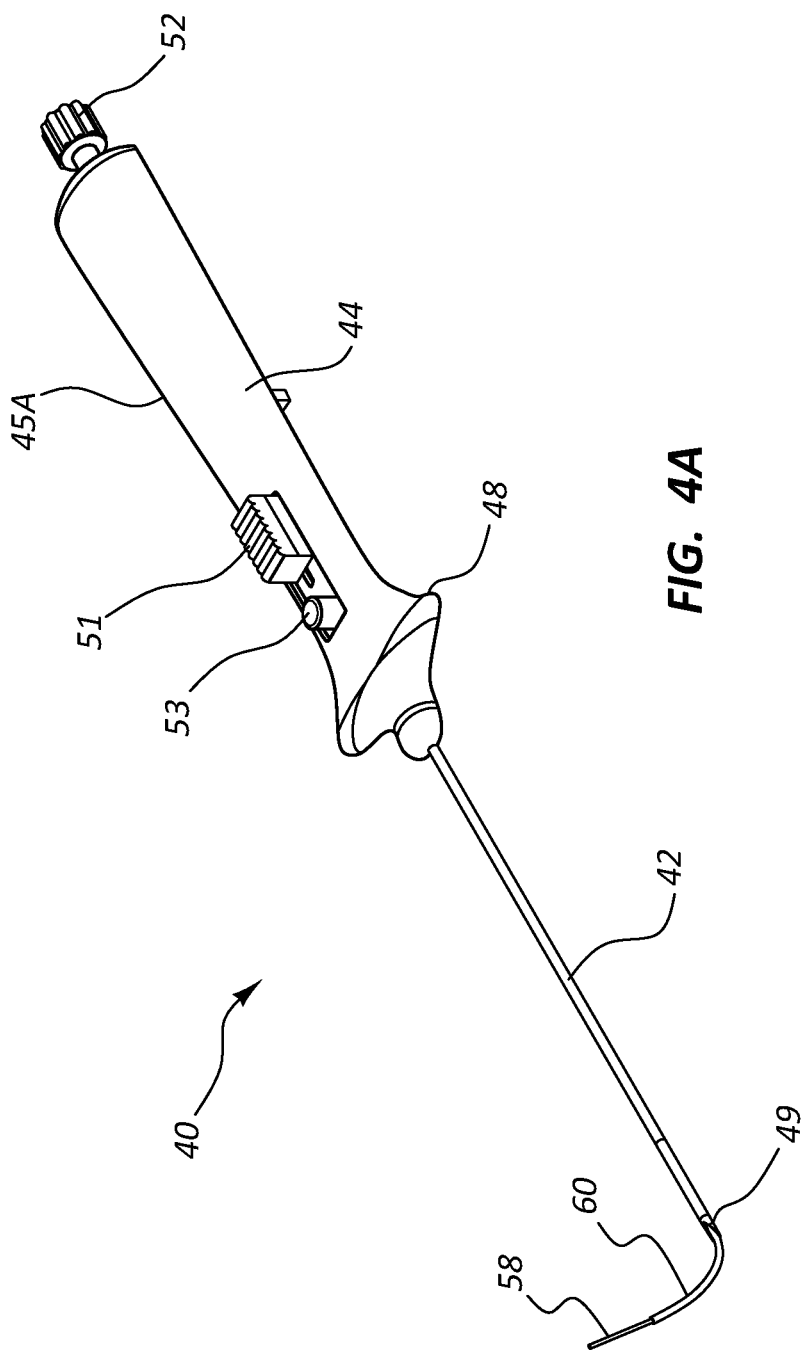
FIG. 4A illustrates a perspective view of the device of FIG. 2.
Figure 4B:
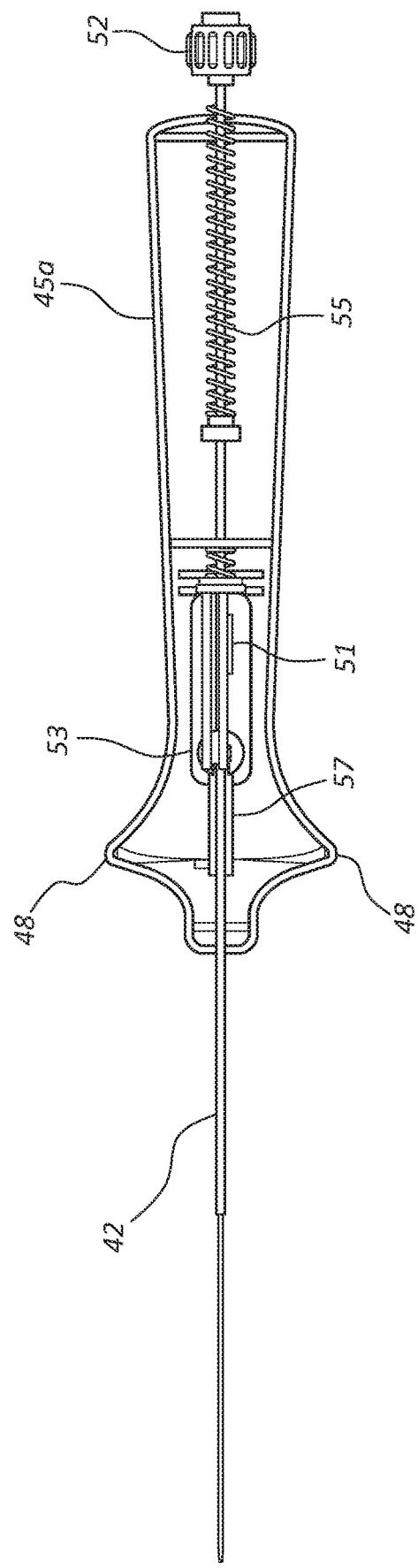
FIG. 4B illustrates a bottom view of the device of FIG. 2 with a top portion removed to expose interior components.
Figure 4C:
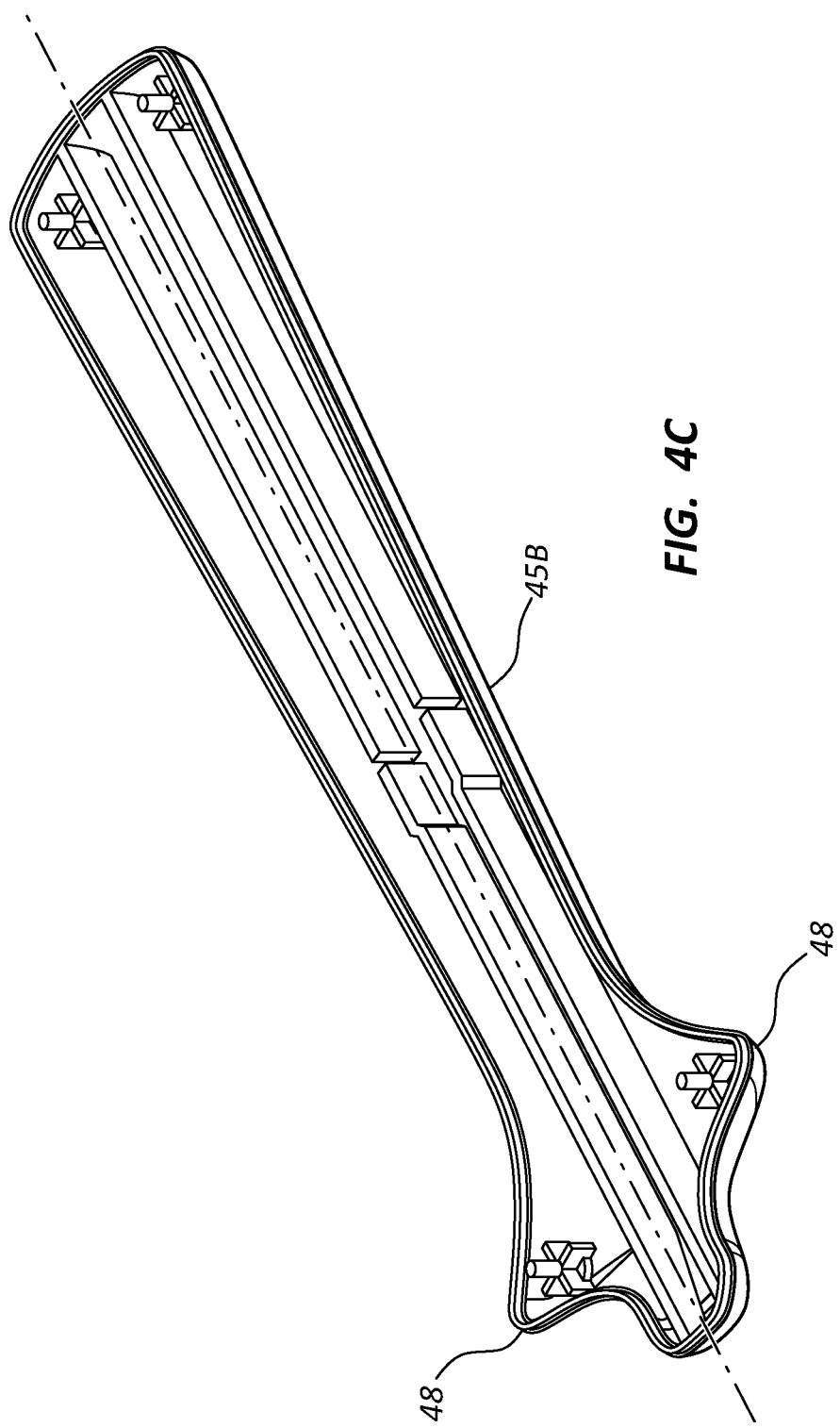
FIG. 4C illustrates a perspective view a bottom portion of the housing of the device of FIG. 2, with other components removed.

The handle 44 may include a top portion 45A and a bottom portion 45B. FIG. 4A is a top perspective view of the top portion 45A of the handle 44 along with other components. FIG. 4B is a bottom view of the top portion 45A of the handle 44, along with other components of the device, with the bottom portion 45B removed to expose internal components. FIG. 4C illustrates a bottom portion 45B of the handle 44. The top portion 45A and the bottom portion 45B may engage to from the handle 44. The handle 44 also includes wings 48 on opposing sides of the handle 44. The wings 48 may be used to apply a distal force to the vascular catheter 42 from the handle 44.

Figure 6A:
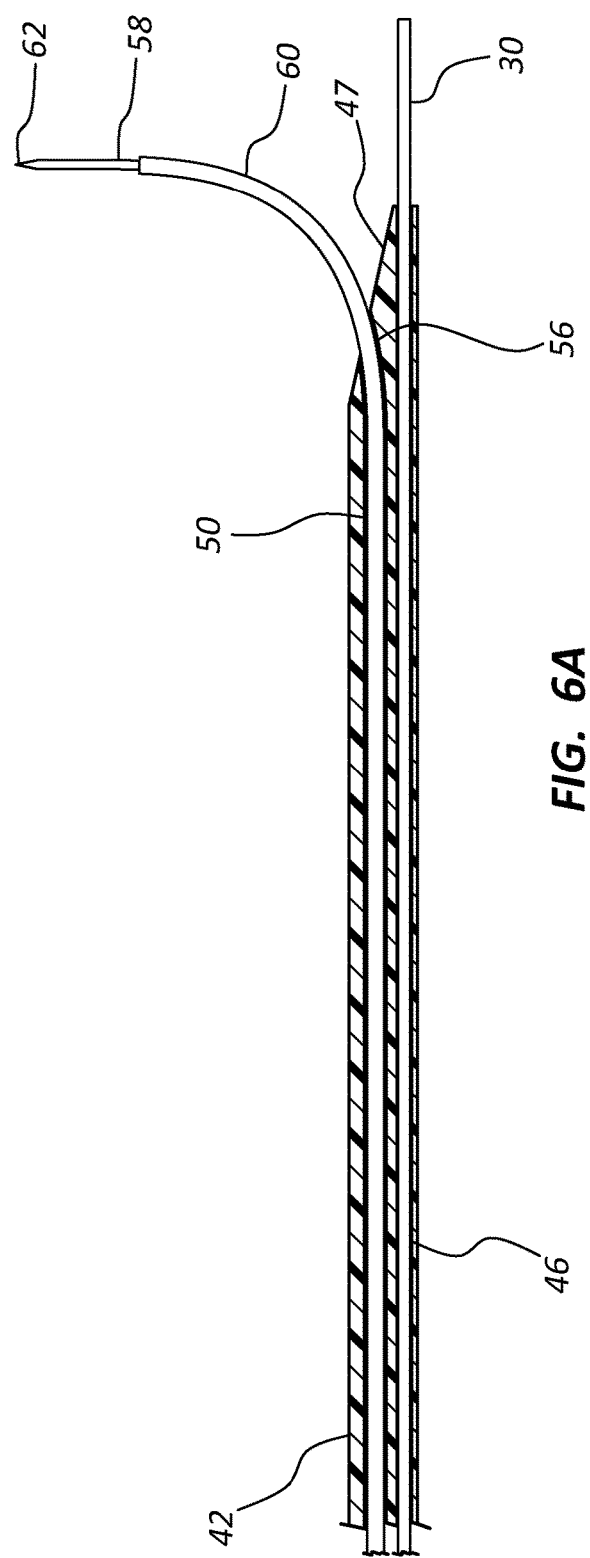
FIG. 6A illustrates a cross-sectional schematic view of a vascular catheter of the device of FIG. 2 in a configuration with the stylet deployed.
Figure 6B:
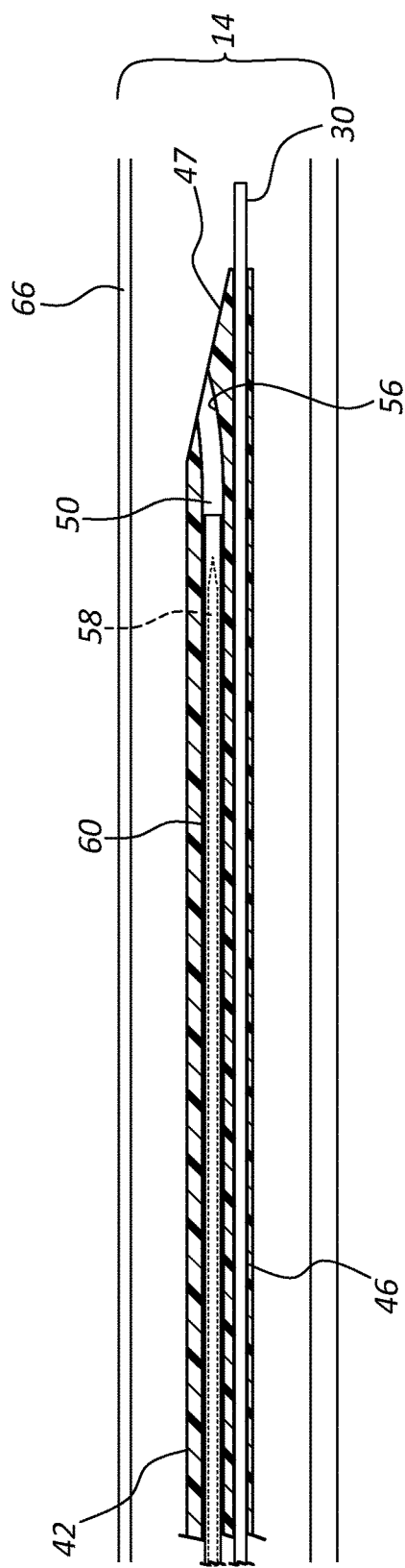
FIG. 6B illustrates a cross-sectional schematic view of the vascular catheter of the device of FIG. 2, in a retracted configuration with the stylet retracted, being advanced over a guidewire in a vessel, such as a vein.

Referring to FIGS. 6A-7B, which illustrate a portion of the access device 40 comprising a distal portion of the vascular catheter 42 in FIGS. 6A and 6B and an analogous portion of an alternative embodiment of an access catheter 42' in FIGS. 7A and 7B. The vascular catheter 42 and 42' are shown in cross-section, while the elements disposed within the access catheters are not in cross-section for clarity. The vascular catheter 42' of FIGS. 7A and 7B is identical to vascular catheter 42 of FIGS. 6A and 6B except that vascular catheter 42' does not comprise a ramped camming surface 56 as detailed below. Accordingly, other elements of the access device 40 of FIG. 2 as shown in FIGS. 7A and 7B (such as guidewire 30) retain the same numerals as the embodiment of FIGS. 2, 6A, and 6B. Disclosure recited in connection with vascular catheter 42 of FIGS. 6A and 6B may be analogously applied to vascular catheter 42' of FIGS. 7A and 7B.

In addition to the guidewire lumen 46, the device 40 may have a stylet lumen 50 extending from the handle 44 to an opening toward the distal end of the vascular catheter 42. In some embodiments, the stylet lumen 50 curves at its distal end to form a camming surface 56, as illustrated in FIGS. 6A and 6B. The camming surface 56 may provide additional structural support to a guide tube or a cover tube 60 when it is in an advanced position. A stylet 58 may be slideably disposed within cover tube 60.

In some embodiments the stylet lumen 50 does not have a curved camming surface 56. For example, the stylet lumen 50 may be substantially cylindrical as illustrated in FIGS. 7A and 7B.

The stylet 58 (formed, e.g., from Nitinol with a diameter of 0.014 inches) enclosed by the cover tube 60 (such as a 0.025 inch diameter Nitinol hypotube) extends from an actuator 51, 52, and 53, in the handle 44 toward the distal end of the device 40. In some embodiments the cover tube 60 has a preformed curved or deflected tip at its distal end. For example, the performed curve may be between 30° and 60° of the longitudinal axis of vascular catheter 42. The optional camming surface 56 may promote the curvature of the cover tube 60.

Stylet 58 may have a sharp distal point 62 adapted to penetrate tissue, such as blood vessels, muscle, and skin. The sharp distal point 62 may be part of a tip designed to have various dimensions and shapes. In some embodiments, the tip 62 may be faceted. For example, the tip 62 may include three flat surfaces that intersect to form a sharp distal point. In some embodiments, tip 62 may be a conical tip. The conical tip may form an angle of about 10° with the shaft of the stylet 58.

Figure 8:
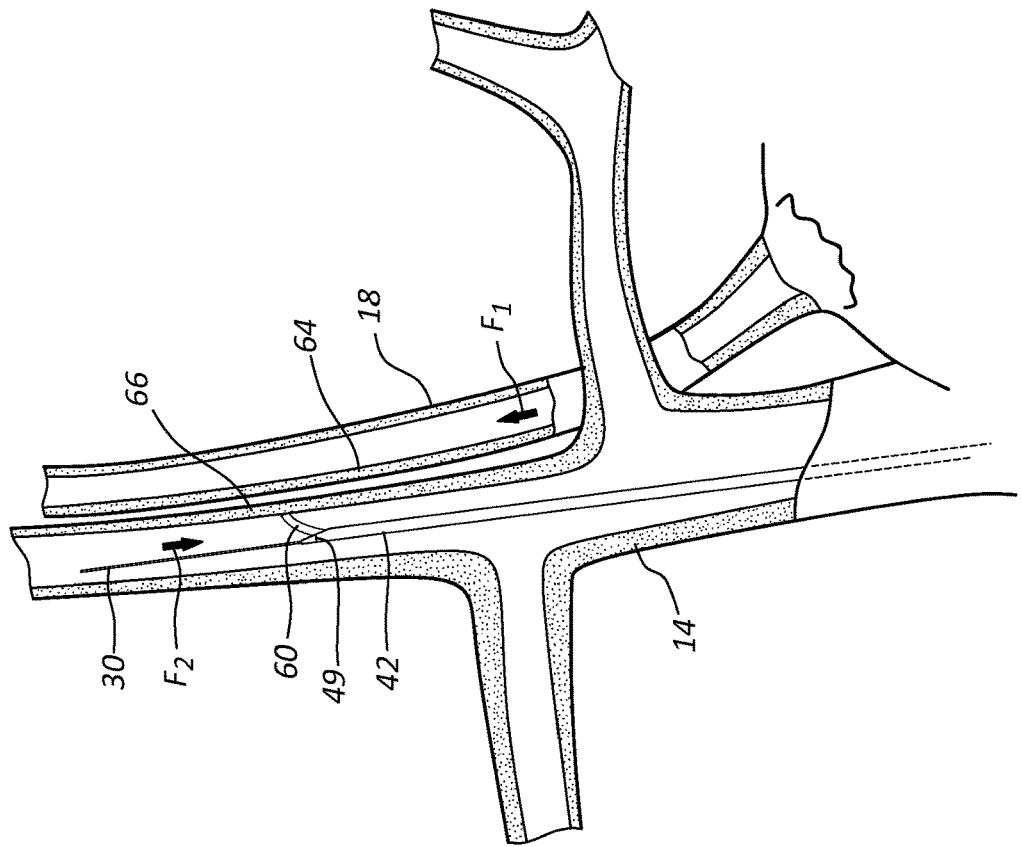
FIG. 8 illustrates a schematic view of the device of FIG. 2 in a retracted configuration, with a vascular catheter in the jugular vein close to an access point for the carotid artery.

To gain access of the carotid artery 18, vascular catheter 40 may be inserted into the femoral vein 12 over the guidewire 30 (with the guidewire disposed as shown in FIG. 1A) and may be advanced adjacent to the desired access point in the jugular vein 14 under fluoroscopic guidance. During this advancement, the stylet 58 and cover tube 60 may be in a retracted configuration, as illustrated in FIG. 8. The distal opening of the stylet lumen 50 may then be oriented toward the desired carotid artery access point in the vein wall 66.

Figure 9:
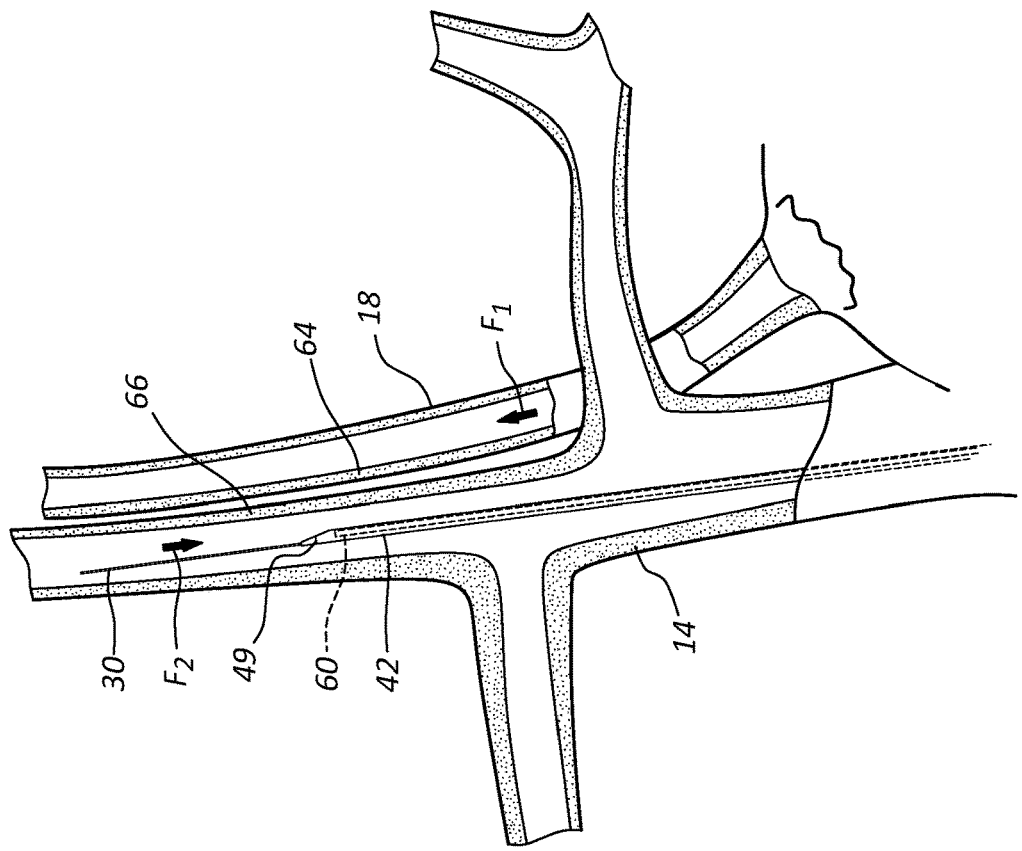
FIG. 9 illustrates a schematic view of the device of FIG. 2 in a primed configuration with the stylet cover tube advanced to a desired access point for the carotid artery.
Figure 10:
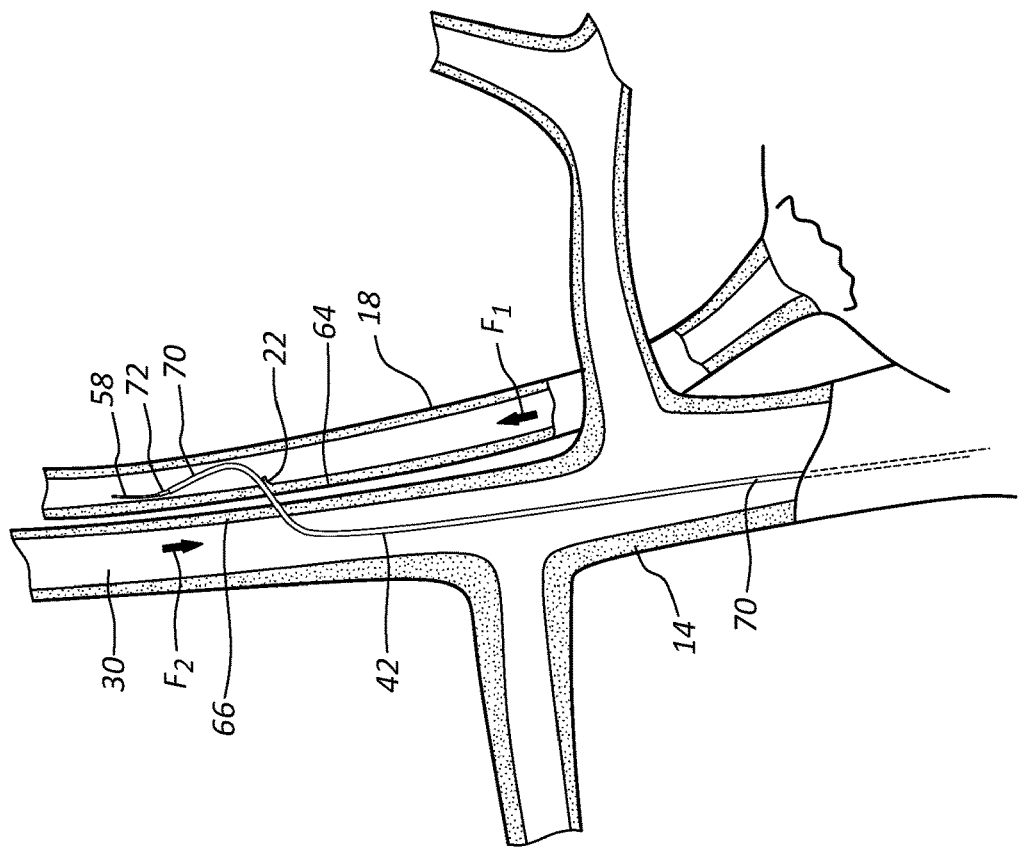
FIG. 10 illustrates a schematic view of the device of FIG. 2 in an actuated configuration with the stylet advanced through the vessel wall of the jugular vein and into the carotid artery.
Figure 11:
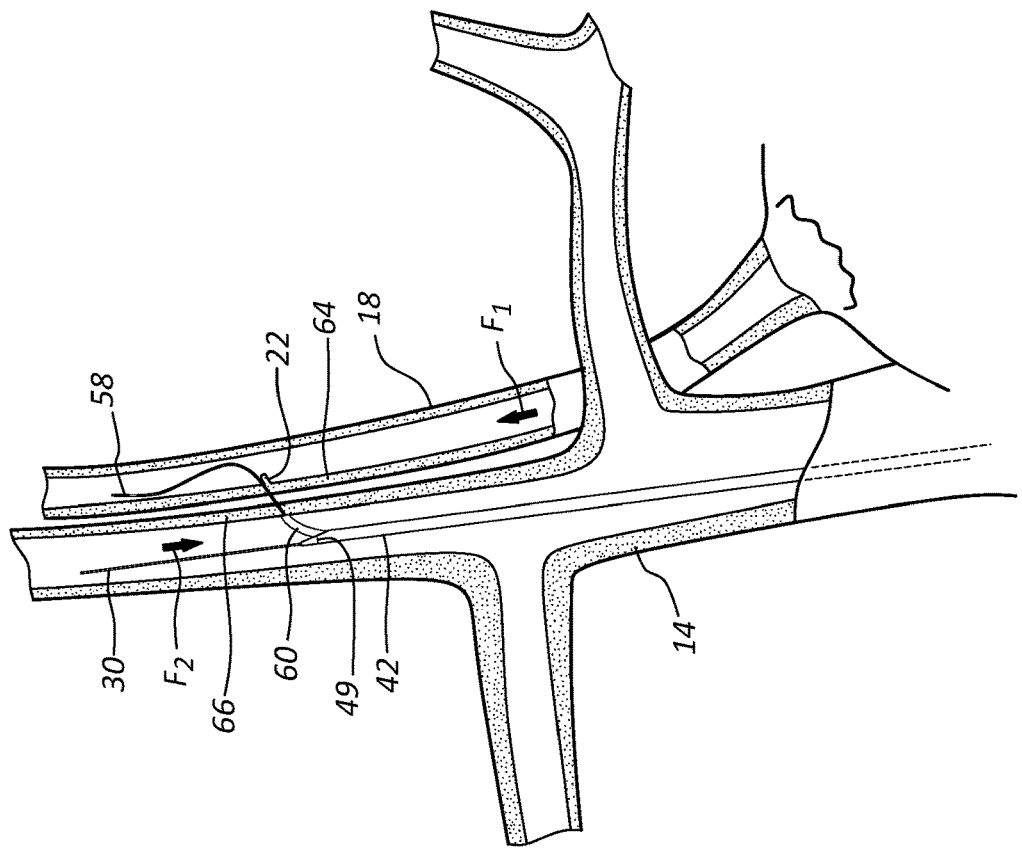
FIG. 11 illustrates a schematic view of the device of FIG. 2 with an access catheter advanced over the stylet.

The arrows ($F_1$ and $F_2$) in FIGS. 8-11 illustrate the direction of blood flow in the jugular vein 14 and the carotid artery 18. The blood in the carotid artery 18 flows away from the heart in direction $F_1$ and the blood flow in the jugular vein 14 flows toward to heart in direction $F_2$. In some embodiments the catheter tip 47 may include a radiopaque marker 49 visible under the fluoroscopy as illustrated in FIGS. 8-10. The radiopaque marker 49 may be embedded in the catheter tip 47. The radiopaque marker 49 is illustrated as a ring in FIGS. 9 and 10; however, other shapes and geometries may be used. In some embodiments the shape of the radiopaque marker 49 may be selected to facilitate fluoroscopic identification of the location and orientation of the catheter tip 47. Examples of radiopaque marker materials include gold, platinum, platinum-iridium, and other biocompatible radiopaque materials.

Figure 5A:
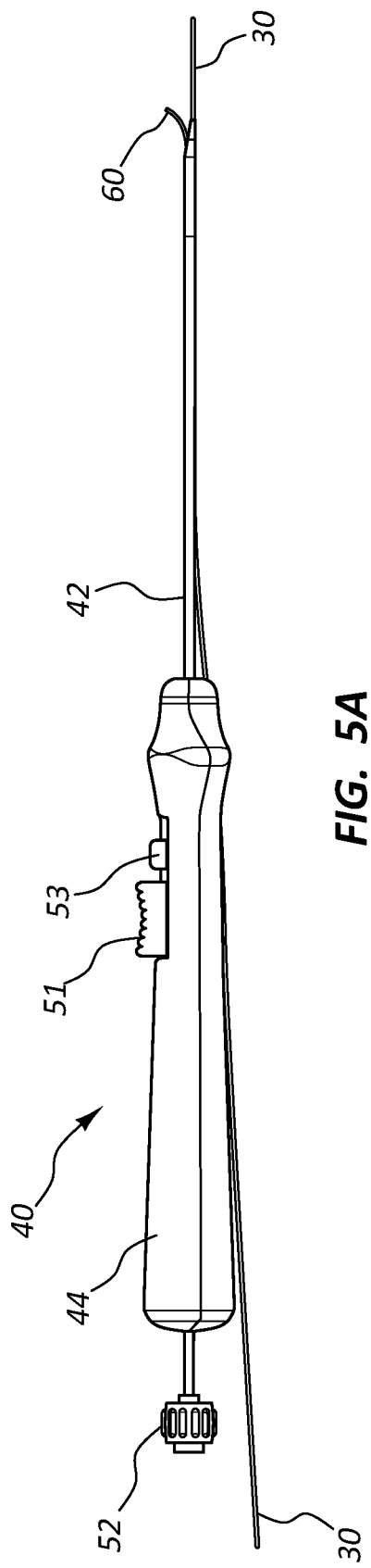
FIG. 5A is a side view of the device of FIG. 2 in a primed configuration with the stylet cover tube advanced and the stylet actuator loaded.
Figure 5B:
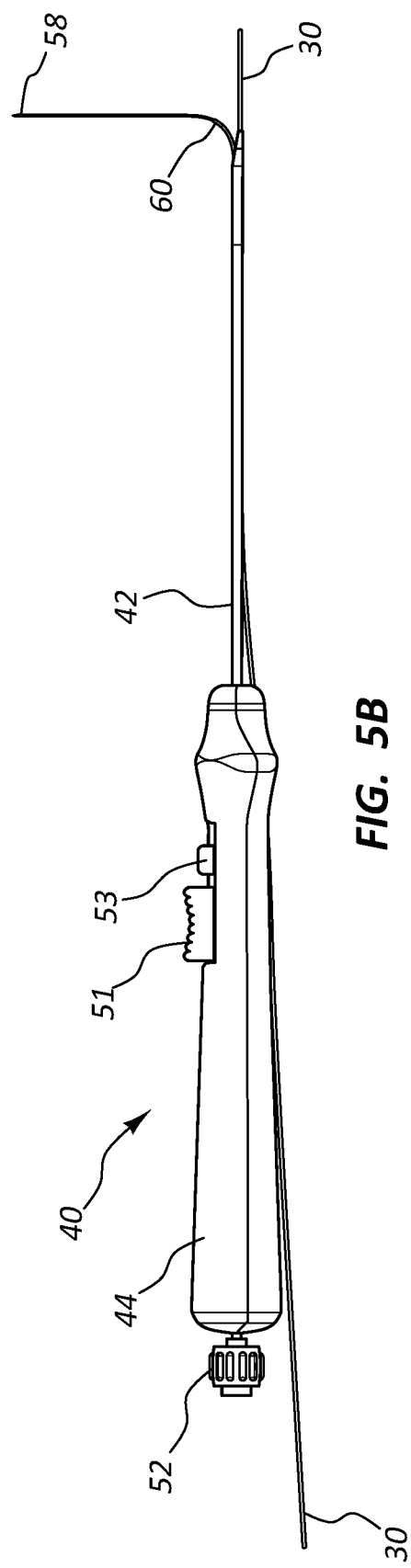
FIG. 5B illustrates a side view of the device of FIG. 2 in an actuated configuration with the stylet deployed.

The cover tube 60 may be advanced out of opening into an primed configuration by moving a slide button 51 proximally in handle 44, at which point the cover tube 60 assumes its curved shape, as shown in FIGS. 5A and 9. In some embodiments, moving the slide button 51 proximally in handle 44 pushes the cover tube distally from the vascular catheter 42. In some embodiments moving the slide button 51 proximally in the handle 44 moves the catheter proximally to expose the distal end of the cover tube 60. As illustrated in FIGS. 4A and 4B, the slide button 51 may engage with and be operatively connected to the vascular catheter 42 with catheter slide 57. In some embodiments, the cover tube 60 is advanced until its distal end is adjacent to the vein wall 66 at the desired carotid artery access point. In some embodiments the cover tube 60 advances until its distal end abuts the vein wall 66 at the desired carotid artery access point. The stylet 58 remains in cover tube 60 in the primed configuration.

The orientation of the extended cover tube 60 may be determined based on the orientation of the handle 44. The slide button 51 engages with the top portion 45A of the handle 44. In the illustrated embodiment, the slide button 51, is disposed substantially perpendicular to a plane defined by the opposing wings 48 that extends along a length of the handle 44 e.g., the plane defined by the curve where the top portion 45A of the handle 44 contacts the bottom portion 45B of the handle 44. The cover tube 60 extends upwards from the stylet lumen 50 and is also substantially perpendicular to the plane defined by the opposing wings 48 extending along a length of the handle 44. The positioning and orientation of the cover tube 60 after it has been advanced may also be visually verified, for example using fluoroscopy prior to deploying the stylet 58. The stylet actuator is loaded by pulling proximally on a spring load mechanism 52 in the handle 44, as illustrated in FIG. 5A. When the slide button 51 is in its proximal position, as illustrated in FIG. 5A, a stylet release button 53 is exposed. Depressing release button 53 advances the stylet 58 distally under the action of a spring 55 to an actuated configuration, as illustrated in FIGS. 5B, 6A, 7A, and 10. The sharp distal tip penetrates the vein wall 66 of the jugular vein 14 and the artery wall 64 of the carotid artery 18, as illustrated in FIG. 10. After the stylet 58 punctures the carotid artery 18, the blood flow $F_1$ of the carotid artery may push the stylet 58 downstream so that it does not damage or perforate the opposing artery wall of the carotid artery 18. The puncture of the artery wall 64 may create a flap 22. The distance traveled by the stylet 58 depends on the application. For example, when the stylet 58 is moving from the jugular vein wall to the carotid artery 18, the stylet 58 may move less than half a centimeter. In other embodiments, the stylet 50 may move more or less than this amount, including 0.25 centimeters or less and 1, 2, 3, 4, or more centimeters.

Various sizes may be used for the cover tube 60. The configuration of the pre-formed cover tube 60 may be varied to use different shapes. The length and pre-formed configuration of the cover tube 60 may be selected based on the size of the vessel to be accessed.

In some embodiments, the cover tube 60 is not fully extended from the vascular catheter 42. For example, the cover tube 60 may not be fully extended to accommodate the specific geometry and size of the vessel. In smaller diameter blood vessels there may not be enough space to fully extend the cover tube; however, the cover tube 60 and stylet 58 may properly function partially extended from the vascular catheter 42.

After the stylet 58 has puncture the carotid artery 18, the guidewire 30, vascular catheter 42, and cover tube 60 may be withdrawn from the jugular vein 14. An access catheter 70 may be introduced and advanced along stylet 58 through the femoral vein 12 to the jugular vein 14 and into the carotid artery 18. Once the access catheter 70 has been introduced into the carotid artery 18, it may be used to perform a number of different medical procedures via the carotid artery 18. Access catheter 70 may advance a particular treatment device or tool 72, for treating the patient. Exemplary treatment devices 72 may include angioplasty balloons, stents, filters, aneurysm stents, etc. These devices 72 may be used to treat a blockage in the carotid artery, treat an embolism in the brain (stroke), treat an aneurysm, place a filter, remove fatty plaque, etc.

Figure 12:
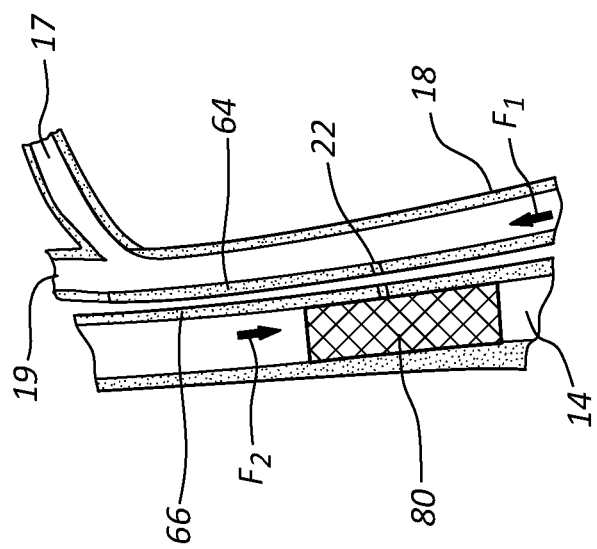
FIG. 12 illustrates a schematic view of a stent to close the opening between the jugular vein and the carotid artery.

After the procedure is concluded, the stylet 58, access catheter 70, and any treatment devices 72 may be withdrawn from the carotid artery 18 and the jugular vein 14. In addition, a closure device 80 may be introduced into the jugular vein 14 adjacent to the opening to close the opening between the jugular vein 14 and the carotid artery 18, as illustrated in FIG. 12. The closure device 80 may be a bioabsorable, tightly meshed/woven venous stent 80. In addition, the opening in artery wall 64 of carotid artery 18 may be closed when the flap 22 is pushed back toward the opening by the blood flow $F_1$ in the carotid artery 18.

FIGS. 13-16 illustrate an alternative method to access the carotid artery 18 of a patient without open surgery and without passing through the aortic arch. The carotid artery 18 may be accessed directly from the patient's neck. For example, under B-mode ultrasound guidance (or fluoroscopy), a puncture needle 10 (e.g., 18 gauge for larger patients, 21 gauge for smaller patients) may be advanced through the skin 90 into the jugular vein 14 and then through the other side of the jugular vein 14 and into the carotid artery 18 at a point below the bifurcation of the carotid artery 18 into the internal carotid artery 19 and the external carotid artery 17. The puncture needle 10 thus creates an opening between the jugular vein 14 and the carotid artery 18 for fluid communication. The puncture needle 10 may also create a flap 22 in the artery wall of the carotid artery 18.

Figure 13:
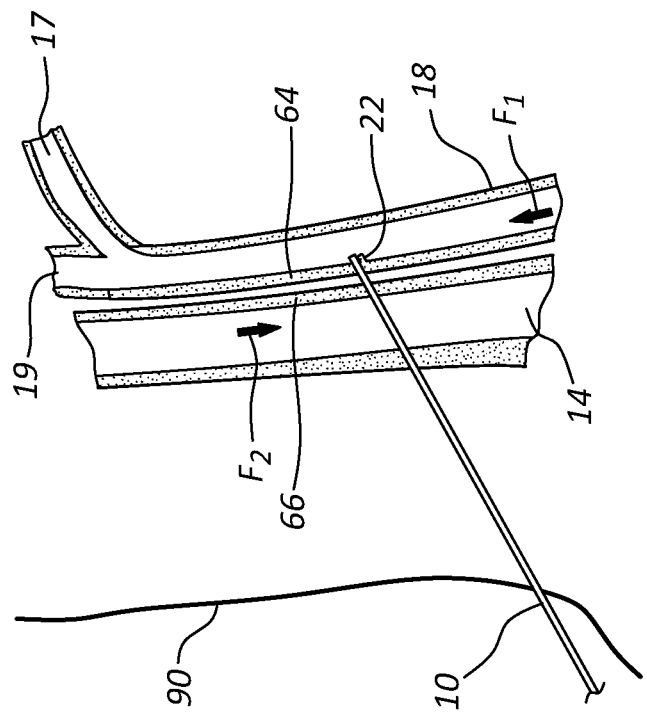
FIG. 13 illustrates a schematic view of a guidewire being introduced into the carotid artery via the puncture needle.

The puncture needle 10 may be inserted at a number of different orientations, for example, at an upward angle, a downward angel, etc. FIG. 13 illustrates the puncture needle 10 being inserted at an upward angle between 30° and 60° off the longitudinal axis of the jugular vein 14. The blood that flows out of the proximal end of the puncture needle 10 may indicate the location of the distal tip 21 of the puncture needle 10. Venous blood from the jugular vein 14 is darker and flows slowly and the higher pressure and more oxygenated arterial blood from the carotid artery 18 flows quicker and is redder than the blood from the jugular vein. This provides another indication to the practitioner that the puncture needle 10 has accessed the carotid artery 18.

Figure 14:
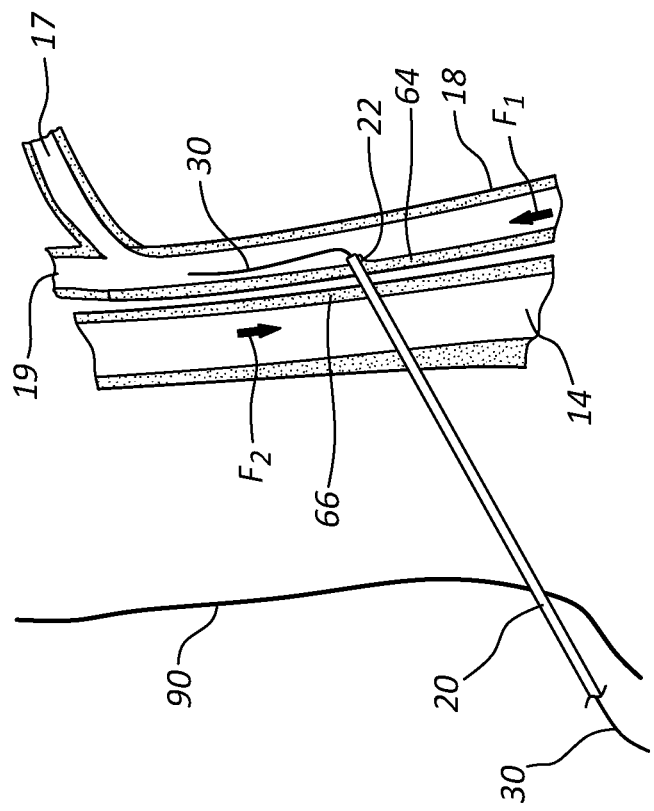
FIG. 14 illustrates a schematic view of a guidewire being introduced into the carotid artery via the puncture needle.
Figure 15:
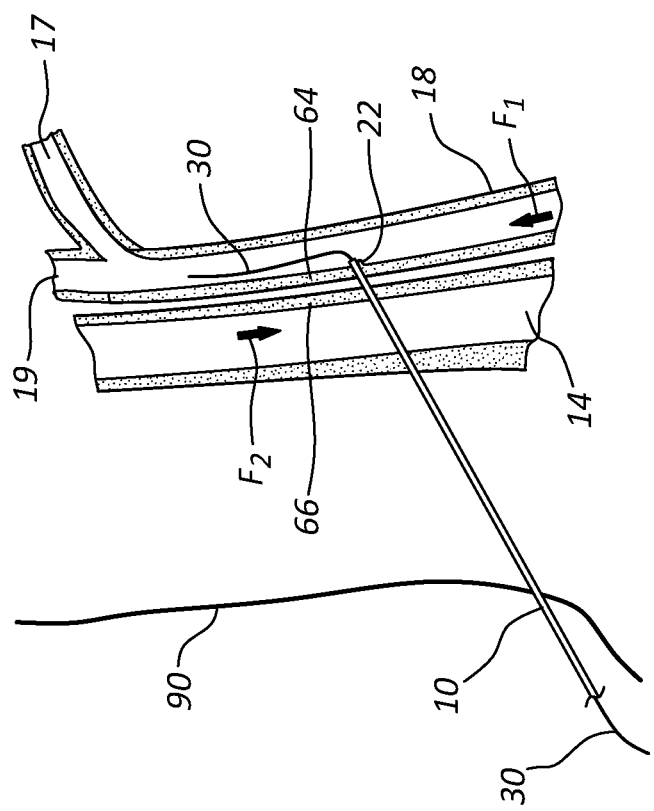
FIG. 15 illustrates a schematic view of an interventional sheath being advanced over the guidewire into the carotid artery.

After the distal tip 21 of the puncture needle 10 is in the carotid artery 18, a guidewire 30 may be advanced through the puncture needle 10 into the carotid artery 18, as illustrated in FIG. 14. After the guidewire 30 is advanced into the carotid artery 18, the puncture needle 10 may be removed and an interventional sheath 26 (e.g., with a diameter of 5 F or 6 F) may be advanced over the guidewire 30, as illustrated in FIG. 15. The interventional sheath 26 may provide access for a catheter or other treatment devices or tools to be advanced into the carotid artery 18 to perform a desired procedure, such as an angioplasty, plaque removal, treat aneurysms, etc. A number of different types of tools, such as angioplasty balloons, filters, stents, etc. may be used.

Figure 16:
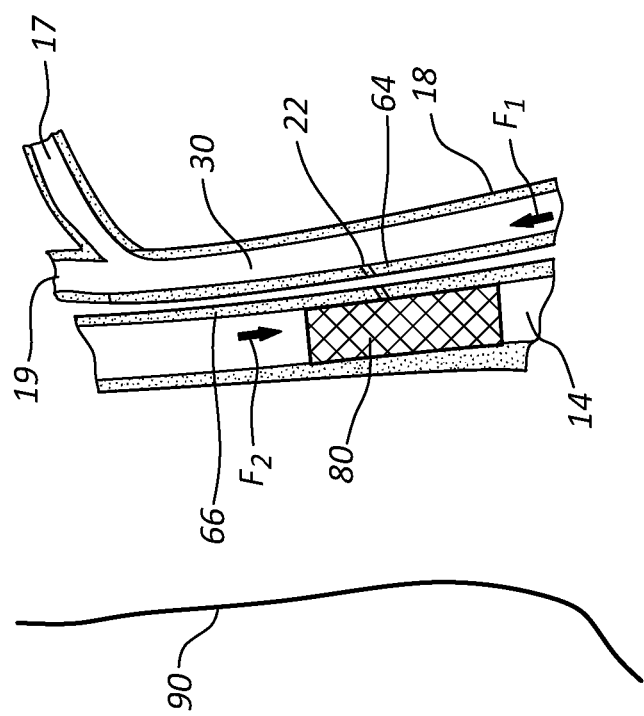
FIG. 16 illustrates a schematic view of a closure device being introduced into the jugular vein to close the opening between the jugular vein and the carotid artery.

After the completion of the carotid artery procedure, a closure device 80 may be introduced into the jugular vein 14 adjacent to the opening to close the opening between the jugular vein 14 and the carotid artery 18, as illustrated in FIG. 16. The closure device 80 may be a bioabsorable, tightly meshed/woven venous stent. In addition, the opening in artery wall 64 of carotid artery 18 may be closed when the flap 22 is pushed back toward the opening by the blood flow $F_1$ in the carotid artery 18.

The closure device 80 may be inserted via the interventional sheath 26 (after it has been withdrawn from the carotid artery 18, but before withdrawing it from the internal jugular vein 14). Alternatively, the closure device 80 may be implanted using a separate catheter (not shown) that has been advanced from a remote entry point in the femoral vein 12 into the jugular vein 14.

Figure 17:
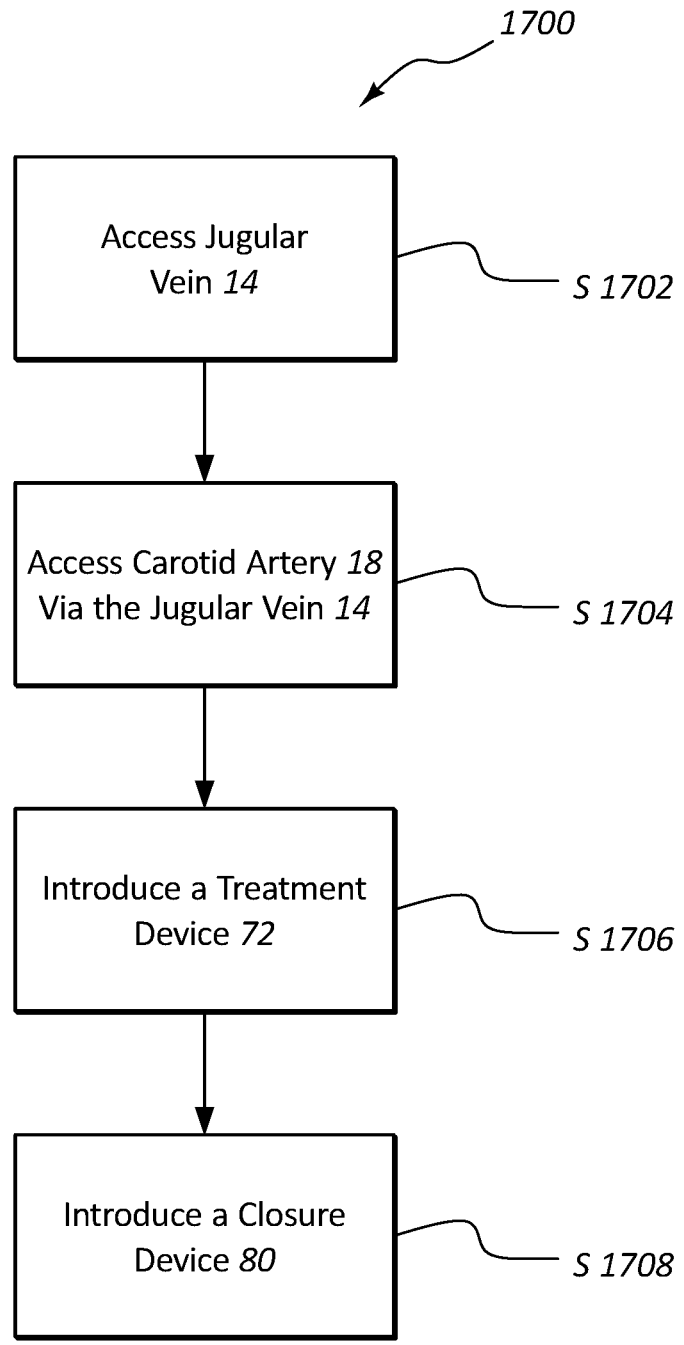
FIG. 17 illustrates a flowchart of a method of accessing a patient's carotid artery through their jugular vein.

FIG. 17 illustrates a flowchart of a method 1700 of accessing a patient's carotid artery 18 via their jugular vein 14, as previously discussed. In step 1702, the practitioner may access the patient's jugular vein 14 in a variety of different manners. For example, as previously discussed, the practitioner may access the jugular vein via a remote access point, such as a femoral vein 12 or a vein 16 in the patient's arm (e.g., brachial vein, basilic vein, cephalic vein, median antecubital, median antebrachial, etc.). Alternatively, the practitioner may access the jugular vein 14 directly by inserting a puncture needle 10 through the patient's neck.

In step 1704, the practitioner may access the carotid artery 18 via the jugular vein 14. For example, as previously discussed, the practitioner may access the carotid artery 18 by piercing the carotid artery 18 after piercing the jugular vein 14 with the puncture needle 10. Alternatively, the practitioner may advance a guidewire 30 and a vascular catheter 42 to the jugular vein 14 and pierce the carotid artery 18 with the stylet 58.

In step 1706, once the practitioner has gained access to the carotid artery 18, the practitioner may introduce or advance a treatment device for treating a medical condition via the carotid artery 18.

In step 1708, after the medical condition has been treated, the treatment device 72 may be removed and the practitioner may introduce a closure device 80 for closing the opening between the jugular vein 14 and the carotid artery 18.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

I claim:

1. A method of accessing a carotid artery of a patient comprising:
    advancing a guidewire to a jugular vein of a patient;
    advancing a catheter along the guidewire to the jugular vein of the patient;
    advancing a cover tube through a lumen of the catheter to a position adjacent a vessel wall of the jugular vein of the patient;
    advancing a stylet through the cover tube; and
    piercing the vessel wall of the jugular vein and piercing a vessel wall of the carotid artery with the stylet to create an opening between the jugular vein and the carotid artery.

2. The method of claim 1, wherein the stylet remains within the carotid artery after piercing the vessel wall of the carotid artery.

3. The method of claim 1, further comprising advancing an access catheter along the stylet to introduce a treatment tool to the carotid artery.

4. The method of claim 3, wherein the treatment tool comprises at least one of an angioplasty balloon, a stent, and a filter.

5. The method of claim 1, further comprising advancing the cover tube out of a distal end of the catheter, wherein the cover tube has a deflecting tip that is aimed toward the carotid artery.

6. The method of claim 1, wherein the stylet pierces the vessel wall of the jugular vein and the vessel wall of the carotid artery at an angle of 30° to 60° off of a longitudinal axis of the catheter.

7. The method of claim 6, wherein a flap is created from piercing the vessel wall of the carotid artery, and
   wherein the flap is configured to bias toward the vessel wall of the carotid artery with the blood flow of the carotid artery.

8. The method of claim 1, wherein the catheter comprises a radiopaque marker and the method is performed using ultrasound or fluoroscopy to advance the catheter to a predetermined position to enable access of the carotid artery via the jugular vein.

9. The method of claim 1, further comprising introducing the guidewire at a femoral vein of the patient and advancing the guidewire to the jugular vein via an inferior vena cava.

10. The method of claim 1, further comprising introducing the guidewire at a brachial vein of the patient and advancing the guidewire to the jugular vein via an inferior vena cava.

11. The method claim 1, further comprising introducing a stent in the jugular vein adjacent to the opening between the jugular vein and the carotid artery to close the opening between the jugular vein and the carotid artery after treatment has been performed.

12. The method of claim 11, wherein the stent is a bioabsorbable mesh.

13. The method of claim 1, wherein piercing the vessel wall of the jugular vein and piercing the vessel wall of the carotid artery with the stylet comprises actuating a stylet actuator to advance the stylet.

14. The method of claim 1, wherein advancing the cover tube comprises proximally moving a slide button of a handle.

15. A method of accessing a carotid artery of a patient comprising:
   obtaining a trans-vascular access devise, comprising:
      a catheter;
      a cover tube disposed within a lumen of the catheter; and
      a stylet disposed within the cover tube;
   advancing a guidewire to a jugular vein of a patient;
   advancing the catheter along the guidewire to the jugular vein of the patient;
   advancing the cover tube through the lumen of the catheter to a position adjacent a vessel wall of the jugular vein of the patient;
   advancing the stylet through the cover tube; and
   piercing the vessel wall of the jugular vein and piercing a vessel wall of the carotid artery with the stylet to create an opening between the jugular vein and the carotid artery.

16. The method of claim 15, wherein piercing the vessel wall of the jugular vein and piercing the vessel wall of the carotid artery with the stylet comprises actuating a stylet actuator to advance the stylet.

17. The method of claim 15, wherein advancing the cover tube comprises proximally moving a slide button of a handle.

18. The method of claim 15, further comprising advancing an access catheter along the stylet to introduce a treatment tool to the carotid artery.

19. The method claim 15, further comprising introducing a stent in the jugular vein adjacent to the opening between the jugular vein and the carotid artery to close the opening between the jugular vein and the carotid artery after treatment has been performed.

\* \* \* \* \*